United States Patent [19]

Taub et al.

[11] Patent Number: 4,806,680

[45] Date of Patent: Feb. 21, 1989

[54] 3-HALOVINYLGLYCINE ANTIBACTERIAL AGENTS

[75] Inventors: David Taub, Metuchen, N.J.; Robert H. Abeles, Newton Centre, Mass.; Arthur A. Patchet, Westfield, N.J.

[73] Assignee: Merck & Co., Inc., Rahway, N.J.

[21] Appl. No.: 119,527

[22] Filed: Nov. 12, 1987

Related U.S. Application Data

[62] Division of Ser. No. 840,254, Mar. 17, 1986.

[51] Int. Cl.$^4$ ............................................ C07C 101/06
[52] U.S. Cl. ..................................................... 562/574
[58] Field of Search ............... 562/574, 553, 556, 560, 562/561, 449; 548/491

[56] References Cited

U.S. PATENT DOCUMENTS 3,960,927  6/1976  Metcalf et al. ...................... 562/561

Primary Examiner—Paul Lieberman
Assistant Examiner—Helene Kirschner
Attorney, Agent, or Firm—Robert J. North; Hesna J. Pfeiffer

[57] ABSTRACT

Described bare 3-halovinylglycines and their amino acid dipeptide and oligopeptide conjugates, a new class of efficient antibacterial agents, pharmaceutical compositions containing them as active ingredients, and methods of synthesis. The compounds are thought to interfere in bacterial cell wall synthesis.

2 Claims, No Drawings

3-HALOVINYLGLYCINE ANTIBACTERIAL AGENTS

This is a division of application Ser. No. 840,254, filed Mar. 17, 1986.

BACKGROUND OF THE INVENTION

1. Field of the Invention

This invention relates to novel 3-halovinylglycines and their amino acid dipeptide and oligopeptide conjugates which display antibacterial activity.

2. Brief Description of Disclosures in the Art

Alanine racemases, which are pyridoxal-requiring enzymes uniquely present in bacteria and essential for biosynthesis of the D-alanine component of the bacterial cell wall, are prime targets for the design of specific inhibitors as new and effective antibacterial agents. In general, the potency of such inhibitors can be correlated with antibacterial activity, assuming effective transport into the bacterial cytoplasm.

Known inhibitors for alanine racemase include cycloserine, 1-aminoethylphosphonic acid, and particularly the β-substituted alanines which are active site directed (suicide type) irreversible inhibitors. For recent reviews see: Neuhaus, F. C.; Hammes, W. P., *Pharmacol. Ther.* 1981, 14, 265–319; Walsh, C. T. *Tetrahedron* 1982, 38, 871–909; and Walsh, C. T. *Ann. Rev. of Biochemistry* 1984, 53, 493–535. Inhibition by the B-substituted alanines is characterized by high partition ratios (ca 800)—that is 800 conversions of inhibitors to pyruvate and reconstitution of active enzyme for every lethal event leading to irreversibly inactivated enzyme. See Wang E.; Walsh, C. T. *Biochemistry* 1978, 17, 1313–1321.

The 3-halovinylglycines are also irreversible inhibitors of alanine racemase and as such interfere with bacterial cell wall biosynthesis. Furthermore, they exhibit low partition ratios (D-3-chlorovinylglycine: partition ratio of about 1) indicative of much greater lethal efficiency in comparison to the β-substituted alanines.

In the literature, new compounds are constantly scrutinized as potential enzyme inhibitors, for example, racemic 3-chlorovinylglycine or 2-amino-3-chloro-3-butenoic acid is described in *Archives of Biochemistry and Biophysics*, Vol. 213, No. 2, February, pp. 695–707 (1982) as not being an inactivator for cystathionine synthetase in the synthesis of cystathionine from serine. However, no discussion of the optically active isomers or their activity as alanine racemase inhibitors is given.

In the field of antibacterial agents, new compounds and classes of chemical agents are constantly being searched for in an effort to obtain more effective, broader spectrum antibacterials, which display less toxic side effects.

What is particularly desired and what is an object of this invention are newer classes of antibacterials which are distinctly efficacious towards infectious gram-positive and various gram negative bacteria.

SUMMARY OF THE INVENTION

It has been found that 3-halovinylglycines are effective inhibitors of alanine racemase and also that they, and especially their amino acid conjugates, exhibit antibacterial activity especially toward gram-positive bacteria and various gram negative bacteria.

In accordance with this invention there is provided a compound, possessing antibacterial activity, of the following formula:

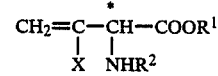
                                      I wherein X is halo (especially F, Cl or Br), $R^1$ is H, and $R^2$ is selected from H or an alpha-amino acid acyl or dipeptide acyl radical. By the term "alpha amino acid acyl or dipeptide acyl radical", as used herein, is meant an acyl radical derived from an alpha amino acid or dipeptide derived from two alpha amino acids, which enhance the transport of the compound into and/or through the bacterial cell wall thus enhancing the antibacterial activity of the compound. Preferred radicals include norvalyl (2-amino-n-pentanoyl), norleucyl (2-amino-n-hexanoyl), methionyl, valyl, leucyl, 2-amino-n-butanoyl, arginyl, lysyl, phenylalanyl, seryl, tryptophanyl, 3-fluorovinylglycyl, 3-chlorovinylglycyl, norvalyl-norvalyl, methionyl-norvalyl, norleucyl-3-chlorovinylglycyl, and D,L stereoisomers and racemates thereof, excluding X=Cl, $R^1 = R^2 = H$ where the compound is a racemate. When $R_1 = H$ and $R_2 = H$ the Zwitterionic structure Ia applies.

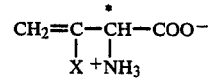
                                      Ia

Further provided is a pharmaceutical composition containing a compound, possessing antibacterial activity, of the following formula:

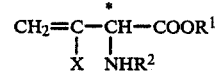

wherein X is halo (especially F, Cl or Br), $R^1$ is H, $R^2$ is selected from H or an alpha-amino acid acyl or dipeptide acyl radical. Preferred radicals include norvalyl, norleucyl, methionyl, valyl, leucyl, 2-amino-n-butanoyl, arginyl, lysyl, phenylalanyl, seryl, tryptophanyl, 3-fluorovinylglycyl, 3-chlorovinylglycyl, norvalyl-norvalyl, methionylnorvalyl, norleucyl-3-chlorovinylglycyl, and D,L stereoisomers and racemates thereof, in an acceptable pharmaceutical carrier.

Also provided is a method of treating bacterial infections (especially gram positive infections) in a mammalian host comprising the step of administering to said host a therapeutically effective amount of a pharmaceutical composition described above-alone or in combination with another antibacterial agent such as cycloserine (pentizidone), fosfomycin, or a β-lactam antibiotic such as ampicillin, cephalexin, cefoxitin, nocardicin, and imipenem.

DESCRIPTION OF THE INVENTION AND PREFERRED EMBODIMENTS

The structure I described above contains a 3-halo substituent wherein X, the halo substituent, is selected from fluoro, chloro, bromo or iodo. A preferred halo substituent is fluoro or chloro and particularly preferred is chloro.

$R^1$ is hydrogen.

R[2] being the substituent on the α-amino group of structure I is selected from hydrogen, an alpha amino acid acyl or dipeptide acyl radical. Representative examples includes norvalyl, norleucyl, methionyl, valyl, leucyl, 2-amino-n-butanoyl, arginyl, lysyl, phenylalanyl, seryl, tryptophanyl, 3-fluorovinylglycyl, 3-chlorovinylglycyl, norvalylnorvalyl, methionyl-norvalyl, norleucyl-3-chlorovinylglycyl, and the like, and D,L stereoisomers and racemates thereof. Preferred R[2] substituents in structure I are norvalyl, and 3-chlorovinylglycyl and particularly preferred is L-norvalyl.

The stereochemistry of structure I arises by virtue of the asymmetric carbon in the α-position which is marked in the structure by an asterisk. Therefore the compound can exist as the D or L form or the racemate form. Preferred stereochemical configuration for compound structure I is the L form when R[2] is not H. When R[2]=H, the D form is preferred.

Specifically excluded from the structures included within the scope of the compound structure I is where X is chloro, and R[1]=R[2]=hydrogen being in the racemate form.

Included within the scope of the invention are mixtures corresponding to different species of formula I, their stereoisomers and racemates thereof.

Representative examples of compounds included within the scope of structure I are D-3-fluorovinylglycine, L-3-chlorovinylglycine, L-3-fluorovinylglycine, DL-3-fluorovinylglycine, D-3-chlorovinylglycine, D-3-bromovinylglycine, L-norvalyl-D,L-3-fluorovinylglycine, L-norvalyl-L-3-fluorovinylglycine, L-norvalyl-D-3-fluorovinylglycine, L-norvalyl-D,L-3-chlorovinylglycine, L-norvalyl-L-3-chlorovinylglycine, L-norvalyl-D-3-chlorovinylglycine, L-3-chlorovinylglycyl-L-3-chlorovinylglycine L-methionyl-L-3-chlorovinylglycine, and the like. Preferred compounds included within structure I are the norvalylchlorovinylglycine compounds and particularly preferred is L-norvalyl-L-chlorovinylglycine.

A method of making compounds included within the scope of formula I where X is specifically chloro and Z is benzyloxycarbonyl is given in the following Flowsheet I.

FLOWSHEET I
Synthesis of 3-Chlorovinylglycine

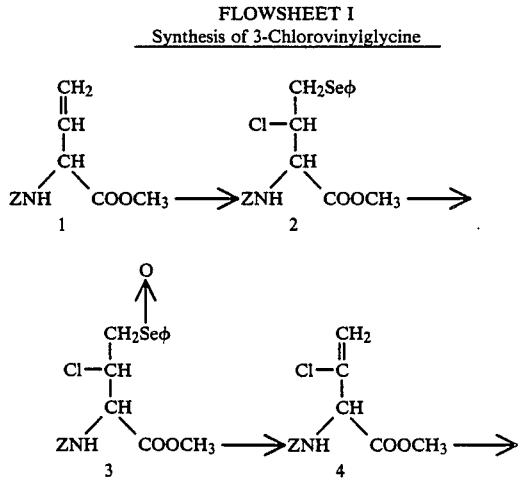

-continued
FLOWSHEET I
Synthesis of 3-Chlorovinylglycine

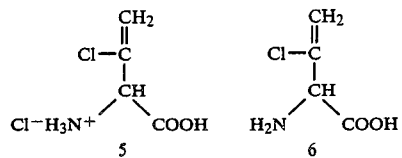

The synthesis of D, L and DL-3-chlorovinylglycine 6 (flowsheet I) can proceed from the corresponding N-benzyloxycarbonylvinylglycine methyl ester 1 which can be obtained from the corresponding D, L or DL-methionine, according to the known procedure of Afzali-Ardakani, A. and Rapoport, H. *J. Org. Chem.* 1980, 45, 4817–4820. The procedure for introducing vinyl halide functionality is based on that of S. Raucher, *Tetrahedron Lett.* 1977, 3909–3912, for conversion of simple 1-alkenes to 2-bromo or 2-chloro-1-alkenes. Both of the above procedures are hereby incorporated by reference for this particular purpose.

Addition of phenylselenenyl chloride across the double bond of 1 ($\phi$SeCl/CH$_3$CN/0°-25°/2 hours) can occur regiospecifically to give adduct 2, in good yield. Of several oxidation procedures (NaIO$_4$, H$_2$O$_2$, O$_3$) ozonization (CCl$_4$/$-20°$) gives the cleanest results. The thermal elimination can be carried out by adding the ozonization reaction mixture (containing 3) to refluxing CCl$_4$ containing one equivalent of pyridine. The thermolysis product 4 can be deprotected to give chlorovinylglycine as the hydrochloride 5. The free amino acid 6 can be obtained by treatment of a methanol solution with propylene oxide or by ion exchange chromatograhpy on Dowex 50 (H+), and eluting with 3% aqueous pyridine.

Similar treatment of 1 with o-nitrobenzeneselenenyl bromide and processing as for 2→6 will yield D, L and DL 3-bromovinylglycine.

A method of preparing compounds of structure I where X is fluoro is given below in Flowsheet II.

FLOWSHEET II
Synthesis of 3-Fluorovinylglycine

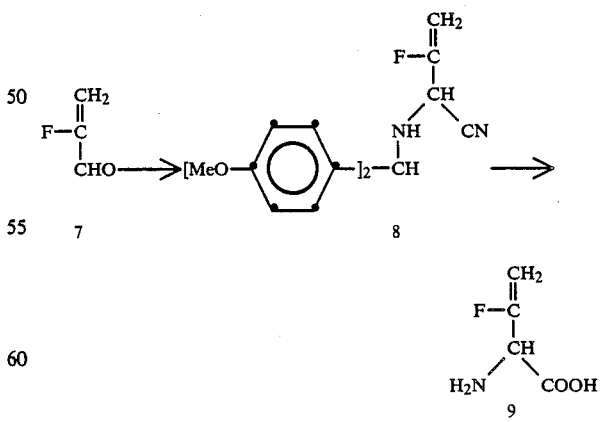

DL 3-fluorovinylglycine 9 (Flowsheet 2) can be obtained in 25-30% yield from 2-fluoroacrolein 7 via Strecker reaction utilizing Greenlee's conditions for conversion of α,β-unsaturated aldehydes into β,r-unsaturated amino acids. See Buddrus, J.; Nerdel, F.;

Hentschel, P.; Klamman, D. *Tetrahedron Lett.* 1966, 5379–5383. Greenlee, W. J. *J. Org. Chem.* 1984, 49, 2632–2634.

Reaction of 7 with 4,4'-dimethoxybenzhydrylamine (4A molecular sieves/$CH_2Cl_2$) followed by addition of trimethylsilyl cyanide occurs mainly in the 1,2 mode leading to aminonitrile 8. Hydrolysis with 6N hydrochloric acid (100°/2 hours) yields the amino acid hydrochloride which can be purified by Dowex 50 ($H^+$) chromatography and elution with 3% aqueous pyridine to yield DL-3-fluorovinylglycine 9.

FLOWSHEET III
Synthesis of Norvalyl 3-Halovinylglycine

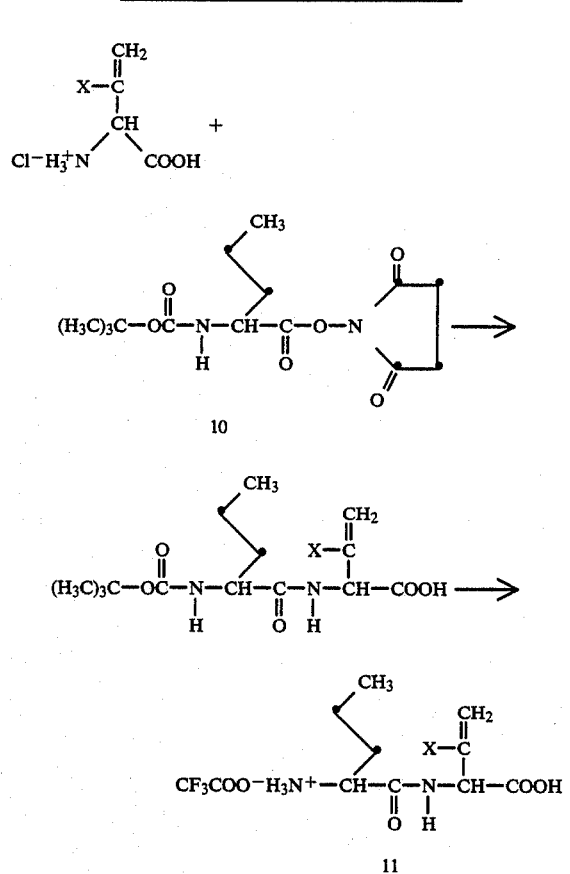

In Flowsheet III is shown the synthesis of compounds of structure I where $R^2$ is other than hydrogen, (for example $R^2$=norvalyl), which can be accomplished by reacting the 3-halovinylglycine (hydrochloride salt or free acid), with N-t-butyloxycarbonylnorvaline N-hydroxysuccinimide 10 followed by deprotection to give the desired peptide product 11. The stereochemistry can be controlled by utilizing either L- or D-3-halovinylglycine and L-or D-norvalyl species to give the desired stereochemistry in the final molecule.

Flowsheet IV illustrates the conversion of DL-fluorovinylglycine (the product of Flowsheet II) to respectively D- and L-fluorovinylglycine.

FLOWSHEET IV
L-3-Fluorovinylglycine and D-3-Fluorovinylglycine

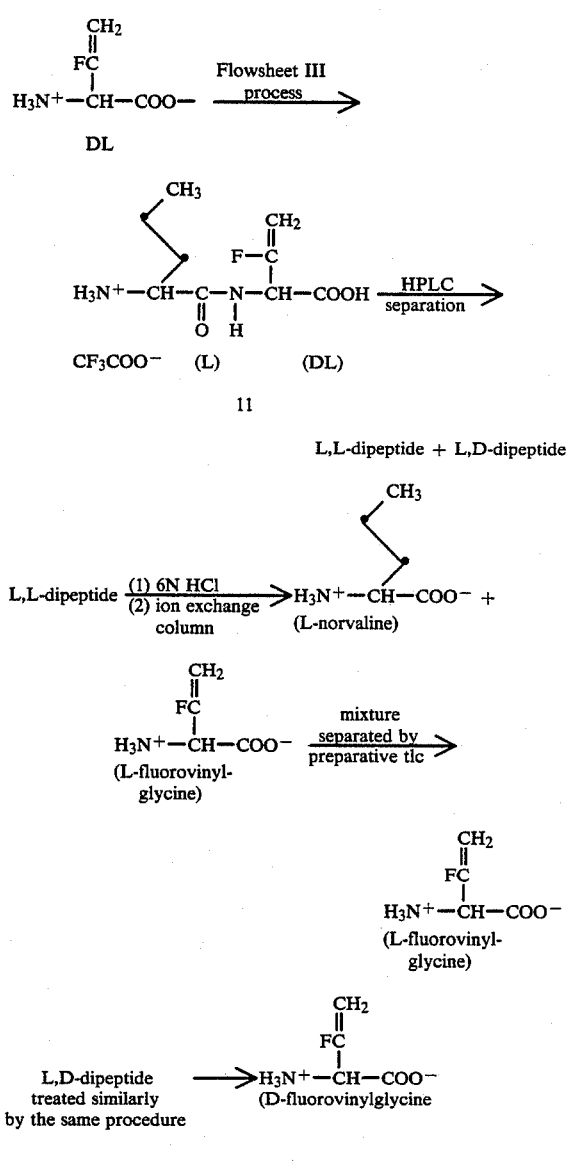

D-and L-fluorovinylglycine (Flowsheet IV) can be obtained by HPLC separation (Zorbax ODS, $H_2O$ elution) of L-norvalyl-DL-fluorovinylglycine (Flowsheet III, X=F) into the individual L,L-and L,D-dipeptides. Each of these can be hydrolyzed (6N HCl/100°/24 hr) and the corresponding L- or D-fluorovinylglycine separated from L-norvaline by preparative tlc on silica gel. Other standard peptide forming procedures can be utilized in carrying out the process of Flowsheet III. Preferred are those in which the carboxyl group of the $R_2$ component is preactivated, for example as the azide, the p-nitrophenyl ester, the mixed anhydride with ethyl carbonate, and the like, for protection of the amino group of $R^2$ the tert-butyloxycarbonyl or benzyloxycarbonyl group are preferred.

The compounds of this invention (I) form a wide variety of pharmacologically acceptable salts with acids at the amine function when $R^2$=H, and of the amino group in certain species of I with functionalized $R^2$. Such pharmaceutically acceptable acid addition salts are derived from organic and inorganic acids such as HCl, HBr, citric, tartaric and the like.

The salts of this invention are pharmacologically acceptable nontoxic derivatives which can be used as the active ingredient in suitable unit dosage pharmaceutical forms. Also, they may be combined with other drugs to provide compositions having a broad spectrum of activity.

The novel compounds of the present invention are valuable antimicrobial substances which are active against various gram-positive and gram-negative pathogens. Thus, the free acid and especially the acid salts thereof such as, those derived form organic and inorganic acids such as HCl, HBr, citric, tartaric, and the like are useful bactericides and can be used for removing susceptible pathogens from dental and medical equipment, for separating microorganisms, and for therapeutic use in humans and animals. These salts can be combined with pharmaceutically acceptable liquid and solid vehicles to form suitable dosage unit forms such as pills, tablets, capsules, suppositories, syrups, elixirs and the like which can be prepared in accordance with procedures well known in this art.

The novel compounds are valuable antibiotics active against various gram-positive and gram-negative bacteria and, accordingly, finding utility in human and veterinary medicine. The compounds of this invention can therefore by used as antibacterial drugs for treating infections caused by gram-positive or gram-negative bacteria, for example against *Staphylococcus aureus, Streptococcus faecalis, Escherichia coli,* and *Klebsiella pneumoniae, Salmonella typhimurium* and *Proteus vulgaris.* The antibacterials of the invention may further be utilized as additives to animal feedstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination with other antibacterial agents such as cycloserine (Pentizidone), fosfomycin, or a β-lactam such as ampicillin, cephalexin, cefoxitin, nocardicin and imipenem and also as an active ingredient in any one of a variety of pharmaceutical preparations. These antibiotics and their corresponding salts may be employed in capsule form or as tablets, powders or liquid solutions or as suspension or elixirs. They may be administered orally, intravenously or intramuscularly.

Tablets and capsules for oral administration may be in unit dose presentation form, and may contain conventional excipients such as binding agents, for example, syrup, acacia, gelatin, sorbitol, tragacanth or polyvinylpyrrolidone; fillers for example, lactose, sugar, maize starch, calcium phosphate, sorbitol or glycine; lubricants, for example, magnesium stearate, talc, polyethylene glycol, silica; disintegrants, for example, potato starch or acceptable wetting agents such as sodium lauryl sulfate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example, methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient, or mixtures thereof, may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semisolid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition there may also be included in the composition other active ingredients to provide a broader spectrum of antibiotic activity.

For veternary medicine the compositions may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 5 to about 600 mg of active ingredient per kg of body weight of the subject in one or more applications per day. A preferred daily dosage for adult humans lies in the range of from about 10 to 120 mg of active ingredient per kg of body weight.

The instant compositions may be administered in several unit dosage forms as, for example, in solid or liquid orally ingestible dosage form. The compositions per unit dosage, whether liquid or solid may contain from 0.5% to 99% of active material, the preferred range being from about 10–60%. The composition will generally contain from 15 mg to about 1500 mg of the active ingredient; however, in general, it is preferable to employ a dosage amount in the range of from about 250 mg to 1000 mg. In parenteral administration the unit dosage is usually the pure compound in a slightly acidified sterile water solution or in the form of a soluble powder intended for solution.

The following examples are illustrative of the claimed invention and should not be construed as being limitations on the scope or spirit thereof.

EXAMPLE 1

2-(D)-Benzyloxycarbonylamino-3-chloro-4-phenyl-selenenylbutyric acid methyl ester 2

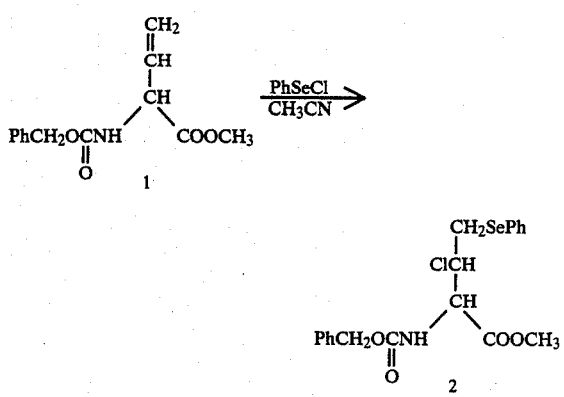

A solution of (D)-N-benzyloxycarbonylvinylglycine methyl ester 1, prepared by the procedure of A. Afzali-Ardakani and H. Rapoport, J. Org.Chem. 45, 4817 (1980), hereby incorporated by reference for this particular purpose containing 2.55 g, (10.2 mmol) in acetonitrile (10 ml), was added dropwise over 15 minutes to a stirred solution of 98% pure phenylselenenyl chloride (2.23 g, 11.4 mmol) in acetonitrile (15 ml) at 0°–5° C. The cooling bath was removed and the mixture was stirred for one hour. The reaction mixture was then concentrated under vacuum and the residue partitioned between chloroform and water. The chloroform layer was washed with dilute aqueous potassium bicarbonate, then saturated aqueous sodium chloride, dried over sodium sulfate and concentrated to dryness to give the 3-chloro-4-phenylselenenyl adduct 2 (4.5 g); tlc-silica gel; hexane:ethyl acetate 4:1, $R_f=0.43$; nmr (CDCl$_3$) $\delta$3.53 (r-CH$_2$, $\beta$-CH), 3.80 (s, OCH$_3$), 5.10 (s, Ph-CH$_2$), 5.2 (d, $\alpha$-CH), 5.5 (d, NH), 7.30 (s, Ph-CH$_2$), 7.5 (m, PhSe).

The corresponding adducts 2 in the (L) and (DL) series were prepared by substantially the same procedure except utilizing (L)-N-Benzyloxycarbonylvinylglycine methyl ester and (DL)-N-Benzyloxycarbonylvinylglycine methyl ester, as the starting reagents, as prepared by the above-cited procedure of A. Afzali-Ardakani and H. Rapoport.

The retention times (tlc) and nmr spectra values are as follows:

(L)2 tlc-silica gel; hexane:ethyl acetate 4:1, $R_f=0.43$; nme (CDCl$_3$) $\delta$3.53 (m), 3.80 (s), 5.10 (s), 5.2 (d), 5.5 (d), 7.3 (s), 7.5 (m).

(DL)2 tlc-silica gel; hexane:ethyl acetate 4:1, $R_f=0.43$; nmr (CDCl$_3$) $\delta$3.53 (m), 3.80 (s), 5.10 (s), 5.2 (d), 5.5 (d), 7.3 (s), 7.5 (m).

In the process of Example 1 the vinylglycine starting material may also be N-protected with other acyl type protecting groups utilized in amino acid chemistry such as the urethane type [4-methoxybenzyloxycarbonyl, 2-chlorobenzyloxycarbonyl, t-butoxycarbonyl], formyl, trifluoracetyl and the like. The carboxyl group may also be protected as an alkyl (ethyl, propyl, t-butyl and the like) or aralkyl (benzyl, 4-methoxybenzyl, 3,4-dimethoxybenzyl, benzhydryl) ester.

In place of phenylselenenyl chloride other arylselenenyl chloride preferably containing electron withdrawing groups such as 2-, 3-, or 4-nitrophenyl- or 2-, 3-, or 4-chlorophenylselenenyl chloride may be utilized.

The reaction may be carried out in an inert solvent in which both reactants are (at least partly) soluble such as chloroform, methylene chloride, ethyl acetate, tetrahydrofuran, and diethylether at a reaction temperature of $-78°$ to $40°$ and a time range of 10 minutes to 20 hours.

EXAMPLE 2

(D)-3-Chloro-N-benzyloxycarbonylvinylglycine methyl ester 4

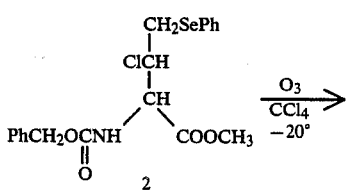

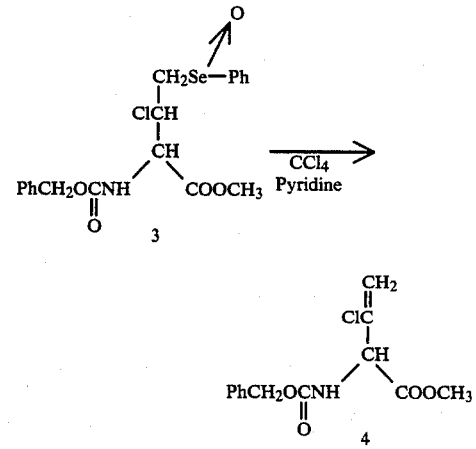

A stirred solution of adduct 2 (4.5 g), from Example 1, in carbon tetrachloride (35 ml) was cooled to $-20°$ C. Ozone in oxygen (generated in a Welsbach ozonizer) was bubbled gently into the above solution for 50 minutes at $-20°$ C., followed by nitrogen to displace remaining ozone. The mixture was warmed to $+20°$ C. and transferred to a dropping funnel. It was then added dropwise over 30 minutes to a stirred gently refluxing solution of carbon tetrachloride (50 ml) and pyridine (0.93 ml). After an additional hour of reflux the mixture was cooled and washed with dilute aqueous potassium bicarbonate, dilute hydrochloric acid, saturated aqueous sodium chloride, dried over sodium sulfate and concentrated to dryness. The residue was chromatographed over silica gel (300 g) eluting with hexane:ethyl acetate-4:1 to give 743 mg of fractions rich in product 4. Rechromatography gave pure 4 (325 mg). Tlc-silica gel-hexane:ethyl acetate-4:1, $R_f=0.47$; $\alpha_D-39.4°$ (C=2.33, CH$_3$OH); nmr (CDCl$_3$) $\delta$3.77 (s, OCH$_3$), 5.07 (d, C$\alpha$-H), 5.10 (s, CH$_2$Ph), 5.47 (d,d, J=2, 8, CH$_2$=C), 5.73 (m, NH), 7.27 (s, PhCH$_2$); ms, M+ 283, 285.

The corresponding compounds 4 in the (L) and (D,L) series were made by substantially the same procedure but utilizing the (L) or (DL) starting materials.

(L) 4 had $\alpha_D+39.3°$ (C=3.67, CH$_3$OH); tlc, hexane:ethyl acetate-4:1, $R_f=0.47$; nmr (CDCl$_3$) $\delta$3.77 (s), 5.07 (d), 5.10 (s), 5.47 (d,d), 5.73 (m), 7.27 (s); ms, M+ 283, 285.

(DL) 4 had tlc, hexane:ethyl acetate-4:1, $R_f=0.47$; nmr (CDCl$_3$) δ3.77 (s), 5.07 (d), 5.10 (s), 5.47 (d,d), 5.73 (m), 7.27 (s); ms, M+ 283, 285.

The ozonization reaction may be carried out in other compatible solvents such as methylene dichloride, chloroform, 1,2-dichloroethane, ethylacetate at a temperature range of −78° to 0°.

Other oxidants may be used instead of ozone to form the arylselenoxide. These include sodium periodate in aqueous methanol, hydrogen peroxide in aqueous acetone or aqueous tetrahydrofuran, m-chlorperbenzoic acid in methylene dichloride, chloroform or tetrahydrofuran.

The selenoxide elimination (olefin forming) reaction may be conducted in an inert solvent other than carbon tetrachloride—such as 1,2-dichloroethane, tetrahydrofuran, ethylacetate at a temperature range from 60° to 100° C.—with 80°±10° preferred.

EXAMPLE 3

(D)-3-Chlorovinylglycine hydrochloride

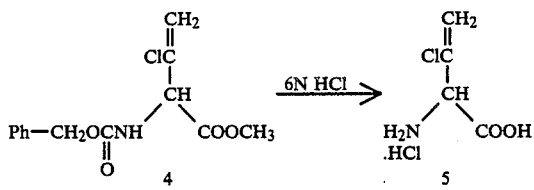

A stirred solution of compound 4 (320 mg) in 6N hydrochloric acid (13 ml) was stirred and refluxed gently for 1 hour. The mixture was cooled and extracted with chloroform. The aqueous layer was treated with charcoal and the colorless filtrate concentrated to dryness. The residue was dissolved in water, reconcentrated to dryness and triturated with acetone to give 5 as a colorless crystalline solid (154 mg, 78%); m.p.>250°; $\alpha_D$−114° (C=1.80, H$_2$O); nmr (D$_2$O) δ4.88 (s, Cα-H), 5.71 (d,d, J=3, 6, CH$_2$=C); ms (TMS) M+ 279, 281; tlc, silica gel, ethyl acetate:n-butanol:acetic acid:water-1:1:1:1 system, $R_f=0.52$.

Anal. for C$_4$H$_6$NO$_2$Cl.HCl: Calcd: C, 27.93; H, 4.10; N, 8.14. Found: C, 28.07; H, 4.12; N, 8.29.

The corresponding compounds 5 in the (L) and (D,L) series were made by substantially the same procedure.

(L) 5 had m.p.>250°; $\alpha_D$+110° (C=1.80, H$_2$O); nmr (D$_2$O) δ4.88 (s), 5.71 (d,d J=3,6); ms (TMS) 279, 281; tlc silica gel, ethyl acetate: n-butanol:acetic acid:water-1:1:1:1 system, $R_f=0.52$;

Anal. for C$_4$H$_6$NO$_2$HCl Calcd: C, 27.93; H, 4.10; N, 8.14. Found: C, 28.47; H, 4.10; N, 8.31.

(DL) 5 had nmr (D$_2$O) δ4.88 (s), 5.71 (d,d J=3, 6); ms (TMS) M+ 279, 281; tlc silica gel, ethyl acetate:n-butanol:acetic acid:water-1:1:1:1 system, $R_f=0.52$.

The free amino acids (D, L, and DL) 6 are obtained by solution of the hydrochlorides 5 (100 mg) in methanol (4 ml), addition of propylene oxide (1 ml) and after 1 hour at 20°–25° C. concentrating to dryness to give 6 as a white solid residue.

Removal of the protecting groups may also be carried out in acetic acid or trifluoroacetic acid saturated with hydrogen bromide or 3–6N aqueous hydrogen bromide at 20°–50° for 1–24 hours.

EXAMPLE 4

(DL) N-(1-Cyano-2-fluoroallyl)-4,4'-dimethoxybenzhydrylamine

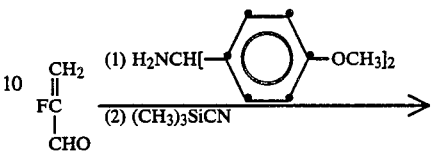

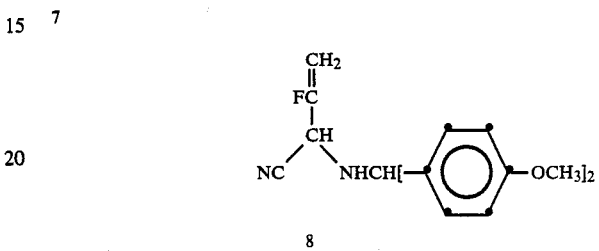

A solution of 2-fluoroacrolein 7, [prepared by the procedure of J. Buddrus, F. Nerdel, P. Hentschel, D. Klamman, Tetrahedron Lett., 5379 (1966) and hereby incorporated by reference for this particular purpose] containing 685 mg, (9.25 mmol) in methylene chloride (1 ml) was added to a stirred solution of 4,4'-dimethoxybenzhydrylamine (2.025 g, 9.25 mmol) in methylene chloride (8 ml). Freshly ground 4A molecular sieves (1.6 g) were added and the mixture stirred one hour at room temperature. Trimethylsilyl cyanide (1.15 g, 11.6 mmol) was added and the mixture stirred 2.5 hours. The mixture was filtered and the filtrate concentrated to dryness to give 8 as a viscous yellow oil (3 g); tlc silica gel, 1% acetone in methylene chloride $R_f=0.66$.

In place of methylene dichloride other suitable solvents include chloroform, 1,2-dichloroethane, tetrahydrofuran. In place of 4,4'-dimethoxybenzhydrylamine other acid hydrolyzable amines such as benzhydryl-, or 3,4-dimethoxybenzylamine may be utilized. The reaction temperature may range from 0° to 40° and the time from 1 to 24 hours.

EXAMPLE 5

(DL)-3-Fluorovinylglycine

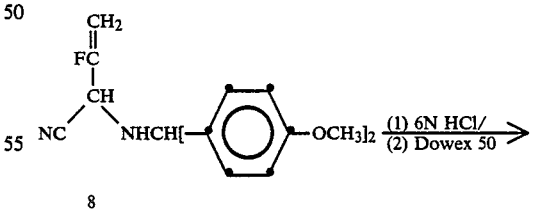

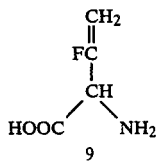

A solution of compound 8 (2.7 g) in 6N hydrochloric acid (33 ml) was stirred and gently refluxed for 2.5 hours. The mixture was cooled, water was added and the resulting mixture extracted with methylene chloride. The aqueous layer was treated with charcoal and the colorless filtrate concentrated to dryness. Trituration with acetone gave a cream colored solid (750 mg). A 500 mg aliquot in 7 ml of water was placed on a column (2×12 cm) of Dowex 50W×4 (H+ cycle) ion exchange resin. Elution with water (500 ml) followed by 3% pyridine in water (375 ml) and concentration to dryness gave fluorovinylglycine 9 (265 mg) as a white solid; tlc-ethyl acetate:n-butanol:acetic acid:water-1:1:0.5:0.5-single spot $R_f$ 0.38. Recrystallization from acetone:water gave 190 mg of transparent rhomboidal plates m.p. 210° (dec); nmr (D$_2$O) $\delta$4.50 (d, $J_{HF}$=26, C$\alpha$-H), 4.74 (d,d, $J_{HH}$=4, $J_{HF}$=25, trans CH=CF), 5.28 (d,d, $J_{HH}$=4, $J_{HF}$=8, cis CH=CF); ms (TMS) M+=263.

Anal. for C$_4$H$_6$NO$_2$F: Calcd: C, 40.34; H, 5.08; N, 11.76; F, 15.95. Found: C, 40.38; H, 5.06; N, 11.72; F, 16.02.

Other conditions for deprotection include saturated hydrogen bromide in acetic or trifluoracetic acids or 3–6N aqueous hydrogen bromide at 20°–50° for 1–24 hours.

EXAMPLE 6

(L,L)-Norvalyl 3-chlorovinylglycine trifluoroacetate

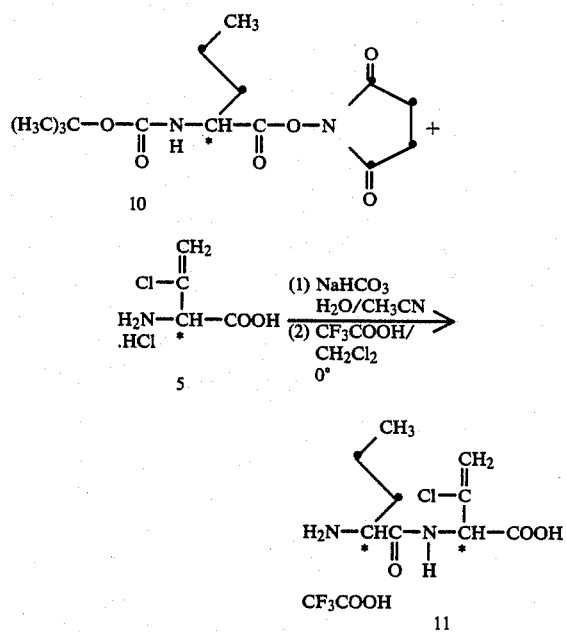

To a stirred solution at 20°–25° C. of (L)-N-t-butyloxycarbonylnorvaline N-hydroxysuccinimide ester 10 (100 mg) prepared by the method of C. W. Anderson, J. E. Zimmerman and F. M. Callahan, J. Am. Chem. Soc. 86, 1839(1964), and (L) 3-chlorovinylglycine hydrochloride 5 (55 mg) in acetonitrile (1.5 ml) and water (1.5 ml) was added 80 mg of powdered sodium bicarbonate. The mixture was stirred 2 hours and concentrated to remove acetonitrile. Saturated aqueous sodium dihydrogen phosphate (20 ml) was added and the mixture was extracted with ethyl acetate (5 times). The ethyl acetate extract was washed with water, saturated aqueous sodium chloride, dried over sodium sulfate and concentrated to dryness to give (L,L) N-t-butyloxycarbonylnorvalyl 3-chlorovinylglycine (115 mg); tlc silica gel chloroform:acetone:acetic acid-85:15:5, $R_f$=0.43.

To the latter was added 4 ml of 1:1 trifluoroacetic acid:methylene chloride at 0°. After 5 minutes the cooling bath was removed and after 40 minutes the mixture was taken to dryness. The residue was dissolved in water, the latter solution charcoaled and the colorless filtrate freeze-dried to give (L,L)-nkorvalyl 3-chlorovinylglycine trifluoroacetate 11 (80 mg) as a white powder; tlc on silica gel, n-butanol:ethyl acetate:acetic acid:water-1:1:0,.5:0.5, $R_f$=0.53; nmr (D$_2$O) $\delta$0.97 (t, J=6, CH$_3$—CH$_2$), 1.40 (m, CH$_3$e,uns/CH$_2$—), 1.82 (m, C$\overline{\text{H}}_3$CH$_2$—CH$_2$—), 4.00 (t, J=6, —CH$_2$—CH—), 5.22 (s, —C—H=C—Cl), 5.45 (d, $J_{HH}$=2 trans C$\overline{\text{H}}$=CCl), 5.55 (d, $J_{HH}$=2 cis CH=CCl); ms (FAB) M+ +H=235, 237.

Utilizing substantially the same procedure were prepared the (L) norvalyl peptides of (D)-3-chlorovinylglycine and (DL)-3-chlorovinylglycine with similar mass spectra as the (L,L) dipeptide. The respective nmr spectra were similar except in the (L,D) dipeptide for a singlet at $\delta$5.27 (instead of 5.22) and in the (L,DL) dipeptide singlets at 5.22 and 5.27. The tlc retention time in the above system of the (L,D) dipeptide was 0.47 and the (L,DL) depeptide showed the two components at $R_f$=0.47 and 0.53.

(L,D) 11 (X=Cl) had tlc, silica gel, n-butanol:ethyl acetate:acetic acid:water-1:1:0.5:0.5 system, $R_f$=0.47; nmr (D$_2$O) $\delta$0.97 (t), 1.40 (m), 1.82 (m), 4.00 (t), 5.27 (s), 5.45 (d), 5.55 (d); ms (FAB) M+ +H=235, 237.

(L,DL) 11 (X=Cl) had tlc, silica gel, n-butanol:ethyl acetate:acetic acid:water-1:1:0.5:0.5 system, $R_f$=0.47, 0.53; nmr (D$_2$O) $\delta$0.97 (t), 1.40 (m), 1.82 (m), 4.00 (t), 5.22 (s), 5.27 (s), 5.45 (d), 5.55 (d); ms (FAB) M+ +H=235, 237.

By the above procedure are also prepared the (L) norvalyl peptides of (D), (L) and (DL) 3-fluorovinylglycine and (D), (L) and (DL) 3-bromovinyl glycine described below.

(L,D) 11 (X=F) had tlc, silica gel, n-butanol:ethyl acetate:acetic acid:water-1:1:0.5:0.5 system, $R_f$=0.48; ms (FAB) M+ +H=219.

(L,L) 11 (X=F) had tlc-same system, $R_f$=0.51; ms (FAB) M+ +H=219.

(L,DL) 11 (X=F) had tlc-same system, $R_f$=0.48, 0.51; ms (FAB) m+ +H=219.

EXAMPLE 7

(L,L)-Norvalyl-3-fluorovinylglycine trifluoroacetate
(L,D)-Norvalyl-3-fluorovinylglycine trifluoroacetate (L,DL)-Norvalyl-3-fluorovinylglycine trifluoroacetate (106 mg) was separated into the (L,L) and (L,D) diastereomers by HPLC on a Zorbax ODS column eluting with water. The (L,L) diastereomer had a retention time of 3 minutes. The (L,D) diastereomer had a retention time of 4 minutes. The stereochemical assignments were based on analogy with the (L,L) and (L,D)-norvalyl 3-chlorovinylglycines. The (L,L)diastereomer is slightly more mobile on tlc (silica gel, ethyl acetate:n-butanol:acetic acid:water-1:1:0.5:0.5 system) and is more active in the antibacterial agar dilution assay [See Example 11].

EXAMPLE 8

L-Fluorovinylglycine and D-Fluorovinylglycine (L,L)-Norvalyl-3-fluorovinylglycine (50 mg) was stirred in 6N hydrochloric acid (acid 4 ml) at 110° C. for 24 hr. and the mixture was concentrated to dryness. The residue [(L)-norvaline and (L)-3-fluorovinylglycine] was separated into its components by preparative thin layer chromatography on silica gel plates (System-1:1:1:1-ethyl acetate:n-butanol:acetic acid:water). The more polar band (UV visualization) was scraped off and eluted from the absorbent with 80% acetonitrile:water and the filtered solution concentrated to dryness under reduced pressure. The residue was dissolved in water. The solution treated with charcoal, filtered and the filtrate freeze dried to yield (L)-3-fluorovinylglycine as a colorless solid tlc 1:1:1:1-ethyl acetate:n-butanol:acetic acid:water $R_f=0.52$; ms (TMS) M+ =263.

Similar treatment of (L,D)-norvalyl-3-fluorovinylglycine afforded D-3-fluorovinylglycine with $R_F=0.52$ (same system) and ms (TMS) M+ =263.

EXAMPLE 9

(D)-3-Bromovinylglycine

Reaction of (D)-N-benzyloxycarbonyl vinylglycine methyl ester with O-nitrophenylselenenyl bromide by the procedure of Example 1 yields (D)-2-benzyloxycarbonyl amino-3-bromo-4-o-nitrophenyselenenylbutyric acid methyl ester. Processing of this intermediate by the procedures of Examples 2 and 3 yields D-3 bromovinylglycine hydrochloride.

(L)- and (D,L)-3-bromovinylglycine hydrochlorides are prepared similarly.

The free amino acids are obtained by treatment of the amino acid hydrochlorides in methanol with propylene oxide as in Example 3.

EXAMPLE 10

Utilizing appropriate standard peptide forming procedures, described in "Peptide Synthesis", M. Bodansky, Y. S. Klausner, and M. A. Ondetti, 1976, J. Wiley and Sons, New York, and incorporated herein by reference, there are prepared the following representative peptides of (L), (D) and (DL) 3-chlorovinylglycine, 3-fluorovinylglycine and 3-bromovinylglycine:
L-methionyl-3-halovinylglycine
L-alanyl-3-halovinylglycine
L-valyl-3-halovinylglycine
L-Leucyl-3-halovinylglycine
L-norleucyl-3-halovinylglycine
L-2-amino n-butanoyl-3-halovinylglycine
L-arginyl-3-halovinylglycine
glycyl-3-halovinylglycine
L-norvalyl-L-norvalyl-3-halovinylglycine
L-alanyl-L-norvalyl-3-halovinylglycine
L-methionyl-L-norvalyl-3-halovinylglycine

EXAMPLE 11

Representative 3-halovinylglycines and amino acid conjugates were tested for antibacterial activity by an agar dilution assay [being an modification of the antagonist-free-medium assay described in: Antimicrobial Agents and Chemotherapy, May 1979, pp 677–683 and pp 684–695]. Compounds assayed include (L) and (D)-3-chlorovinylglycine (HCL salts), (L) norvalyl-(L), (D), and (DL)-3 chlorovinylglycine (CF$_3$COOH salts), and (L) norvalyl-(L), (D), and (DL)-3 fluorovinylglycine (CF$_3$COOH) salts.

The antibacterial activity of the representative structure I compounds versus eleven representative strains of pathogenic bacteria is shown in the following Table. The most active compounds are L-norvalyl L-3-chlorovinylglycine and L-norvalyl-3-fluorovinylglycine which show activity vs 8 of 11 and 9 of 11 test species respectively.

D-3-chlorovinylglycine also exhibits antibacterial activity vs *S. aureus, Strep. faecalis, E. coli* and *K. pneumoniae,* and is a potent irreversible inhibitor of *E. Coli* alanine racemase with a partition ratio close to 1.

L-3-chlorovinylglycine also exhibits antibacterial activity vs. *S. Aureus, Strep. faecalis* and *K. pneumonia,* and also inhibits *E. coli* alanine racemase.

| | Agar Dilution Assay [minimum inhibitory concentration (M.I.C.)-mg/ml] | | | | | | | |
|---|---|---|---|---|---|---|---|---|
| Microorganism | (L)-NVA—(DL)-F—vinylgly | (L)-NVA—(L)-F—vinylgly | (L)-NVA—(D)-F—vinylgly | (L)-NVA—(DL)-Cl—vinylgly | (L)-NVA—(L)-Cl—vinylgly | (L)-NVA—(D)-Cl—vinylgly | (D)Cl vinylgly | (L)Cl vinylgly |
| S. aureus | 1.0 | >256 | >256 | ≦0.25 | 0.5 | 16 | 32 | 128 |
| Strep. faecalis | >256 | 64 | " | 4 | 4 | 128 | 64 | 128 |
| E. coli TEM 2+ | 128 | 16 | " | >256 | 8 | 256 | >256 | >256 |
| E. coli DC2 | 4 | 2 | " | 4 | 1 | 32 | 256 | >256 |
| E. coli | 8 | 4 | " | 128 | 32 | >256 | 256 | >256 |
| Sal. typhimurium | 256 | 128 | " | 256 | 64 | >256 | >256 | >256 |
| Ent. cloacae P99− | 64 | 32 | " | >256 | >256 | 256 | >256 | >256 |
| K. pneumoniae | 128 | 2 | " | 32 | 2 | 64 | 128 | 256 |
| Prot. vulgaris | >256 | 32 | " | 256 | 256 | >256 | >256 | >256 |
| Ps. aeruginosa | >256 | >256 | " | >256 | >256 | >256 | >256 | >256 |
| Ser. marcescens | 256 | 64 | " | >256 | >256 | >256 | >256 | >256 |

M.I.C. equal to or less than 256 indicates antibacterial activity

What is claimed is:

1. A process for preparing D-, L- or DL-3-halovinylglycine compounds of the following formulas:

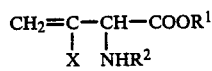

where X is halo, $R^1$=H, $R^2$=H comprising the steps of contacting an N-protected D-, L- or DL-vinylglycine ester with an arylselenenyl halide, oxidizing the adduct to the corresponding selenenyl oxide, thermolyzing the latter to yield the corresponding-N-protected 3-halovinylglycine ester, deprotecting the latter by treatment with mineral acid to yield the corresponding 3-halovinylglycine, as the acid salt, and converting to the free amino having the above formula by treatment with propylene oxide in methanol.

2. A process for preparing DL-3-fluorovinylglycine comprising the steps of contacting 2-fluoroacrolein with an acid hydrolyzable aralkylamine and trimethylsilyl cyanide, hydrolyzing the formed aralkylamino nitrile in mineral acid, and isolating the product by sulfonic acid type ion exchange column chromatography.

* * * * *

UNITED STATES PATENT AND TRADEMARK OFFICE
CERTIFICATE OF CORRECTION

PATENT NO. : 4,806,680

DATED : February 21, 1989

INVENTOR(S) : David Taub, Robert H. Abeles and Arthur A. Patchett

It is certified that error appears in the above—identified patent and that said Letters Patent is hereby corrected as shown below:

IN THE CLAIMS:

Claim 1, line 60, Column 16, insert the word "acid" after amino and before having.

Signed and Sealed this

Sixteenth Day of January, 1990

Attest:

JEFFREY M. SAMUELS

Attesting Officer    Acting Commissioner of Patents and Trademarks